United States Patent [19]

Hwan et al.

[11] Patent Number: 5,527,970
[45] Date of Patent: *Jun. 18, 1996

[54] SYNTHESIS OF ETHYL T-BUTYL ETHER FROM T-BUTANOL IN ONE STEP USING ACID CATALYSTS

[75] Inventors: Rei-Yu J. Hwan, Sugar Land; John F. Knifton, Austin; Brian L. Benac, San Marcos, all of Tex.

[73] Assignee: Texaco Chemical Inc., White Plains, N.Y.

[*] Notice: the term of this patent shall not extend beyond the expiration date of Pat. No. 5,387,722.

[21] Appl. No.: 382,707

[22] Filed: Feb. 2, 1995

[51] Int. Cl.⁶ .............................. C07C 41/09; C07C 43/04
[52] U.S. Cl. ............................................................. 568/698
[58] Field of Search ................................................. 568/698

[56] References Cited

U.S. PATENT DOCUMENTS 5,387,722  2/1995  Knifton et al. .......................... 568/698

*Primary Examiner*—José G. Dees
*Assistant Examiner*—Dwayne C. Jones
*Attorney, Agent, or Firm*—James L. Bailey; Kenneth R. Priem; Cynthia L. Hunter

[57] ABSTRACT

Disclosed is an improved process for preparing ethyl t-butyl ether in one-step which comprises reacting tertiary butanol and ethanol in the presence of a catalyst consisting essentially of a macroreticular acid resin or a pentasil zeolite at a temperature of about 40°–140° C. and atmospheric pressure to about 500 psig.

19 Claims, 10 Drawing Sheets

Fig. 1

Actual variables:
X = Temperature
Y = EtOH:TBA

Actual constants:
LHSV = 2.00

Fig. 2

Actual variables:
X = Temperature
Y = EtOH:TBA

Actual constants:
LHSV = 2.00

Fig. 3

Actual variables:
X = Temperature
Y = EtOH:TBA

Actual constants:
LHSV = 2.00

Fig. 4

Actual variables:
X = Temperature
Y = H2O Level

Actual constants:
LHSV = 1.00
EtOH:TBA = 1.50

Fig. 5

Actual variables:
X = Temperature
Y = H2O Level

Actual constants:
LHSV = 1.00
EtOH:TBA = 1.50

Fig. 6

Actual variables:
X = Temperature
Y = EtOH:TBA

Actual constants:
LHSV = 1.00
H2O Level = 1.00

Fig. 7

Actual variables:
X = Temperature
Y = EtOH:TBA

Actual constants:
LHSV = 1.00
H2O Level = 1.00

Fig. 8

Actual variables:
X = Temperature
Y = EtOH:TBA

Actual constants:
LHSV = 1.00
H2O Level = 1.00

Fig. 9

Actual variables:
X = Temperature
Y = EtOH:TBA

Actual constants:
LHSV = 1.00
H2O Level = 3.00

*Fig. 10*

Actual variables:
X = Temperature
Y = EtOH:TBA

Actual constants:
LHSV = 1.00
H2O Level = 5.00

SYNTHESIS OF ETHYL T-BUTYL ETHER FROM T-BUTANOL IN ONE STEP USING ACID CATALYSTS

CROSS-REFERENCE

This application is related to pending U.S. Ser. No. 08/279,057. It is also related to U.S. Pat. Nos. 4,822,921; 4,827,048; 5,099,072; 5,081,318; 5,059,725; 5,157,162; 5,162,592; 5,157,161; 5,183,947; 5,214,217; 5,214,218; 5,220,078, U.S. Pat. No. 5,387,772, all of which are incorporated by reference herein in their entirety.

FIELD OF THE INVENTION

This invention concerns an improved process for preparing ethyl tertiary butyl ether (ETBE) in one step by the reaction of tertiary butanol and ethanol in the presence of a macroreticular acid resin catalyst or acidic zeolite catalyst. The invention is especially advantageous in that the ethyl tert-butyl ether can be prepared continuously in 40–70% yield and 65–95% selectivity in one step using low temperatures.

The tert-butyl alcohol need not be dehydrated to isobutylene in a separate reactor prior to the reaction with ethanol to form ethyl tertiary butyl ether.

The process can be run with water in the feed, making the rigorous drying of the feed (and/or recycle streams) unnecessary.

BACKGROUND OF THE INVENTION

Ethyl tertiary butyl ether has long been recognized as a suitable blending cosolvent for hydrous ethanol in gasoline stocks. See U.S. Pat. No. 4,207,076, for example, where ETBE has been blended into a fuel gasoline at about a 10 to 20 volume percent level, usually nearer 9 to 10%, in which the fuel comprises about 70 to 84% gasoline and 5 to 20% of 95% ethanol, i.e. grain alcohol. ETBE solubilizes grain alcohol in gasoline in all proportions thereby allowing a wide latitude in the precise amount of ethanol which can be blended with gasoline.

There has been considerable interest in the use of ethyl tertiary butyl ether (ETBE) as a lead free octane booster for gasoline. Note, for example, the following publications: Iburra et al., "Getting the Lead Out With Ethyl t-Butyl Ether," CHEM TECH, Feb. 1988, pp. 120–122 and Verbanic, "ETBE: Ethanol's Motor Fuel Hope?" CHEMICAL BUSINESS, Oct. 1988, at pp. 38–39 and the paper presented at the DeWitt Petrochemical Review, Houston, Texas, March 28–30, 1989, by Neerlich et al., entitled "Huels/UOP Technology for ETBE/MTBE Production." Recently, there has been increased interest in ETBE due to efforts in Washington D.C. to extend tax credits for corn-based ethanol used to produce ETBE.

It is known in the art to produce ETBE or MTBE by reacting isobutylene with either ethanol or methanol, resulting in the formation of ETBE or MTBE, respectively. The reaction normally is conducted in liquid phase with relatively mild conditions. The isobutylene can be obtained from various sources, such as naphtha cracking, catalytic cracking, etc. The resulting reaction product stream contains the desired MTBE or ETBE, as well as unreacted isobutene and other $C_4$ hydrocarbons and methanol or ethanol.

A number of U.S. patents and allowed U.S. applications assigned to Texaco Chemical Inc. disclose methods of making alkyl tertiary alkyl ethers, including ETBE, in one step.

In U.S. Pat. No. 4,822,921, there is described a method for preparing alkyl tertiary alkyl ethers, including ETBE, which comprises reacting a $C_1$–$C_6$ primary alcohol with a $C_{1-C10}$ tertiary alcohol over a catalyst comprising an inert support impregnated with phosphoric acid.

U.S. Pat. No. 4,827,048 describes a method for preparing alkyl tertiary alkyl ethers from the same reactants using a heteropoly acid on an inert support.

U.S. Pat. No. 5,099,072 discloses a method for preparing alkyl tertiary alkyl ethers, including ETBE, over an acidic montmorillonite clay catalyst which possesses very specific physical parameters.

U.S. Pat. No. 5,081,318 discloses a method for preparing alkyl tertiary alkyl ethers by reacting a $C_1$–$C_6$ primary alcohol with a $C_4$–$C_{10}$ tertiary alcohol over a catalyst comprising a fluorosulfonic acid-modified zeolite.

U.S. Pat. No. 5,059,725 discloses a method for preparing alkyl tertiary alkyl ether, including ethyl tertiary butyl ether, from $C_1$–$C_6$ primary alcohols and $C_4$–$C_{10}$ tertiary alcohols over a catalyst comprising ammonium sulfate or sulfuric acid on a Group IV oxide.

U. S. Pat. No. 5,157,162 discloses a fluorosulfonic acid-modified clay catalyst for the production of ETBE, inter alia, from $C_1$–$C_6$ primary alcohols and $C_4$–$C_{10}$ tertiary alcohols.

In U.S. Pat. No. 5, 162,592 there is described a method for producing alkyl tertiary alkyl ethers from $C_1$–$C_6$ primary alcohols and $C_4$–$C_{10}$ tertiary alcohols using a multimetal-modified catalyst.

A hydrogen fluoride-modified montmorillonite clay catalyst is employed in U.S. Pat. No. 5,157,161 to produce alkyl tertiary alkyl ethers, including ETBE.

In U.S. Pat. No. 5,183,947 fluorophosphoric acid-modified clays are employed as catalysts in a method to produce alkyl tertiary alkyl ethers.

In U.S. Pat. No. 5,214,217 there is disclosed the use of a super acid alumina or a faujasite-type zeolite to produce alkyl tertiary alkyl ethers.

U.S. Pat. No. 5,214,218 discloses the use of a haloacid-modified montmorillonite clay catalyst to convert $C_1$–$C_6$ primary alcohols and $C_4$–$C_{10}$ tertiary alcohols to alkyl tertiary alkyl ethers.

Fluorophosphoric acid-modified zeolites are employed in U.S. Pat. No. 5,220,078 to produce alkyl tertiary alkyl ethers.

U.S. Pat. No. 5,243,091 discloses a method for continuous manufacture of MTBE from tertiary butyl alcohol and methanol using a peroxide contaminated feed wherein the peroxide contaminants are decomposed, then charged to a methyl tertiary butyl ether etherification reaction zone with methanol to form an isobutylene-containing MTBE etherification product that is substantially free from peroxide contaminants, wherein the byproduct isobutylene is utilized downstream of the etherification reaction zone as an extractant in the purification of MTF'E and wherein by-product isobutylene is used as a reactant in the preparation of additional MTBE.

Other references in the art which disclose ETBE as a product usually require two stages rather than one and use isobutylene as a reactant.

U.S. Pat. Nos. which discuss the production of ETBE as well as MTBE include:

5,070,016
4,440,063
4,962,239
4,015,783

These patents all use isobutylene as the coreactant rather than t-butanol.

In U.S. Pat. No. 4,334,890, a mixed $C_4$ stream containing isobutylene is reacted with aqueous ethanol to form a mixture of ethyl tertiary butyl ether (ETBE) and tertiary butyl alcohol (tBA).

U. S. Pat. No. 5,015,783 describes a process for producing ethers, including ETBE, which comprises passing a feed stream to an etherification zone, passing the etherification zone effluent stream to a distillation column and further involves cooling the overhead stream, refluxing and recycling.

In U. S. Pat. No. 5,248,836 there is disclosed a process for selective etherification of isobutylene with EtOH to form ETBE in a distillation column reactor containing a fixed bed acid cation exchange resin as a catalytic distillation structure in a reaction distillation zone combined with a straight pass fixed bed reactor.

A process for the production of ETBE and/or MTBE is disclosed in U.S. Pat. No. 2,480,940.

U.S. Pat. No. 5,292,964 discloses a process for production of methyl tertiary butyl ether or ethyl tertiary butyl ether which comprises reacting tertiary butyl alcohol with a lower alcohol selected from methanol or ethanol in an etherification zone and forming an etherification effluent containing lower alkyl tertiary butyl ether, water of reaction and lower alcohol, passing the etherification effluent to a distillation zone and distilling the effluent from the first step to separate an overhead mixture of ether and lower alcohol substantially free of water from a bottoms comprised of tertiary butyl alcohol, lower alcohol and water; and reacting a lower alcohol/ether admixture from said overhead mixture with isobutylene in a second etherification zone to form lower alkyl tertiary butyl ether.

Macroreticular Acid Resins

Acid resin catalysts are known in the art. They are discussed, for example in U.S. Pat. Nos. 4,629,710 and 3,862,258, incorporated herein by reference.

Acidic cation exchange resins are used in U.S. Pat. No. 4,504,687 in a method for producing tertiary ethers from $C_4$ or $C_5$ streams containing isobutene and isoamylene respectively in a process wherein the acidic cation exchange resin is used as the catalyst and as a distillation structure in a distillation reactor column, wherein the improvement is the operation of the catalytic distillation in two zones at different pressures.

Pentasil Zeolites

The characteristic structures of catalytically important molecular sieve zeolites are discussed in "Molecular Sieve Catalysts," by J. Ward, Applied Industrial Catalysis, Vol. 3, Ch. 9, p. 271 (1984). Molecular sieve zeolites which have been investigated in most detail are those which have achieved industrial application, namely, X, Y, mordenite, the pentasil types and erionite.

The pentasil family of zeolites contains a continuing series of which ZSM-5 and ZSM-11 are end members. See T. E. Whyte et al. "Zeolite Advances in the Chemical and Fuel Industries: A Technical Perspective," CATAL. REV.-SCI. ENG., 24,(4), 567–598 (1982).

The article by J. W. Ward, supra, presents an excellent review of pentasil type zeolites. The pentasils usually have a Si/Al ratio greater than 10. A more detailed description of pentasil zeolites follows under the "Description of the Catalyst."

A good overview of applications for zeolites, including pentasil type zeolites is found in an article titled, "Zeolite Catalysts Face Strong Industrial Future", European Chemical News, 10 Jul. 1989, p. 23. For example, medium pore H-ZSM-5 is sometimes added to a zeolite Y catalytic cracking catalyst to increase the aromatics content and hence motor octane, of the gasoline fraction. In the limited space of ZSM-5, where two pore systems of about 5–6 Å in diameter intersect to give spatial regions of around 9 Å diameter at the intersections, there is a cutoff around $C_{10}$ to $C_{11}$ for products from transformation of a wide range of feedstocks, including alkanes, olefins and alcohols.

ZSM-5 is a catalyst used for converting methanol to gasoline, processing C–8 streams, selectively isomerizing m-cresol to p-cresol, suppressing the formation of diphenylalanine in the production of aniline, and producing pyridine and β-picoline from acetaldehyde, formaldehyde and ammonia.

In an Article titled "Shape Selective Reactions with Zeolite Catalysts", J. CATAL., 76, 418 (1982), L. B. Young et al. report data on selectivity in xylene isomerization, toluene-methanol alkylation, and toluene disproportionation over ZSM-5 zeolite catalysts. Some of the ZSM-5 zeolites in this study were modified. It was demonstrated that appropriately modified ZSM-5 class zeolites are capable of generating uniquely selective compositions. Intrinsic reactivities and selectivities are considerably altered with these modified catalysts.

There is a discussion of the shape selective properties of ZSM-5 in "A Novel Effect of Shape Selectivity: Molecular Traffic Control In Zeolite ZSM-5", by E. G. Derouane, et al., J. CATAL., 65, 486 (1980) Some of the observations included the following: (i) linear aliphatics diffuse rather freely in the ZSM-5 framework and can be adsorbed in both channel systems; (ii) isoaliphatic compounds experience stearic hinderance which may restrict their diffusion in the sinusoidal channel system; and (iii) aromatic compounds and methyl substituted aliphatics have a strong preference for diffusion and/or adsorption in the linear and elliptical channels.

E. G. Derouane et al. studied shape selective effects in the conversion of methanol to higher hydrocarbons and alkylation of p-xylene on pentasil-family zeolites. Some of these zeolites were modified by the incorporation of phosphorous, or embedded in a silica filler. Their findings are reported in "Molecular Shape Selectivity of ZSM-5, Modified ZSM-5 and ZSM-11 Type Zeolites", in FARADAY DISCUSSIONS 72, 331 (1981)

It has been reported in the art that methyl t-butyl ether could be prepared from isobutylene over zeolite catalysts.

P. Chu et al. report results of one study in "Preparation of Methyl tert-Butyl Ether (MTBE) over Zeolite Catalysts", IND. ENG. CHEM. RES., 26, 365 (1987). They reported that ZSM-5 and ZSM-11 have been identified to be highly selective zeolite catalysts for the preparation of MTBE from isobutylene. Compared to the conventional commercial catalyst, AMBERLYST® 15 resin, the pentasil zeolites are thermally stable, give no acid effluent and are less sensitive to the methanol-to-isobutene ratio. The excellent selectivity is believed to be effected by the size of their pore structure, which provides easy access to methanol and restricted access to isobutene. In contrast, small pore zeolites such as synthetic ferrierite were found inactive. Large pore zeolites, such as high-silica mordenite and zeolite Beta were not expected to exhibit shape selectivity.

Another reference which discusses the use of pentasil zeolites in MTBE service is by G. H. Hutchings, et al., CATAL. TODAY, 15, 23 (1992).

There remains in the art a need for a method of producing ethyl tertiary butyl ether from ethanol and tert-butanol in one-step which avoids dehydration of isobutylene in a separate process. It would constitute a great advance in the art if it were possible to accomplish the conversion in one step while, at the same time obtaining 40–70% yield of ETBE and high selectivity from ethanol continuously. It would also be advantageous if such a process and the advantages mentioned could be accomplished at a low temperature.

SUMMARY OF THE INVENTION

In accordance with certain of its aspects, the novel method of this invention for preparing ethyl tert-butyl ether (ETBE) from tertiary butyl alcohol and ethanol in one-step comprises reacting tertiary butyl alcohol and ethanol in the presence of a catalyst comprising a macroreticular acid resin catalyst or an acidic pentasil zeolite.

DESCRIPTION OF THE INVENTION

Preparation of the product of this invention may be carried out typically by reacting tertiary butyl alcohol and ethanol in the presence of an etherification catalyst. The etherification is carried out in one-step and the catalyst preferably comprises a macroreticular acid resin or an acidic pentasil zeolite.

The reaction can be represented by the following:

(Eq. 1)

Generally the ethanol and t-butanol coreactants may be mixed in any proportion in order to generate the desired ethyl t-butyl ether (ETBE), but preferably the molar ratio of ethanol to t-butanol (TBA) in the feed mixture should be between 10:1 and 1:10, if the yield of desired ETBE is to be maximized. In order to achieve maximum selectivity to ETBE, and optimum conversion per pass, an excess of ethanol in the liquid feed is desirable. The most preferred ethanol-to-tertiary butanol molar ratio is from 1:1 to 4:1.

The synthesis of Eq. 1 can also be conducted where the t-butanol and ethanol reactants are mixed with certain other components including water, ketones such as acetone and methyl ethyl ketone (MEK), peroxides, such as t-butylhydroperoxide and di-t-butylperoxide, and allyl t-butylperoxide, as well as secondary alcohol such as isopropanol. The fact the process can be run with water in the feed makes rigorous drying of the feed feed (and/or recycle streams) unnecessary. However, the lower the concentration of water, the greater the tert-butanol conversion. Typically each of said classes of components makes up less than 10% of the total feed mixture.

The instant one-step process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with t-butanol would yield methyl tert-butyl ether (MTBE), while reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

In one embodiment of the process of the instant invention for manufacturing ETBE the catalyst is a macroreticular acid resin catalyst.

The macroreticular acid cation exchange resins particularly useful in the present invention are characterized by acidity capacities of 4–6 meq/g, high porosity, high surface area, and less than about 0.5 milliequivalents of H ion per square meter of surface area. The cation exchange resin can contain water, generally from about 0.5 to about 55% by weight. The macroreticular resins utilized in the process of this invention are characterized by the presence of sulfonic acid functionalized groups and a structure having a high degree of true porosity while possessing rigidity and being subject to minimum volume change when immersed or removed from solvents or solutions. Particularly favored are acidic resins with uniform bead size. The preferred bead size is in the 400–800 micron range.

Any suitable solid resin acidic etherification catalyst may be used for this purpose. Suitable resins are typified by the presence of a sulfonic acid groups, e.g., the sulfonated styrene divinyl benzene copolymer exchange resins such as sulfonated cross linked styrene polymers, phenol formaldehyde sulfonic acid resins, benzene-formaldehyde-sulfonic acid resins and the like.

These include resins under the trade names of, for example, AMBERLITE® and AMBERLYST® (Rohm & Haas Co), DOWEX® (Dow Chemical Co.), PUROLITE® (Purolite Co.), Chempro (Chemical Processing Co.), Katalysator (Bayer A.G.), and the like. The preferred resins are strongly acidic ion exchange resins having acidity capacities of 4–6 meq/g, consisting essentially of sulfonated polystyrene, such as a divinyl benzene cross-linked polystyrene matrix containing from about 0.5 to about 20% of copolymerized divinyl benzene. Resins of this nature are manufactured and sold commercially under various trade names such as "DOWEX® 50", "Nalcite HCR" and "AMBERLYST® 15". The use of a catalyst of this type is described, for example, in U.S. Pat. No. 4,144,138 to Rao et al.

Examples 1 through 9 of the instant invention demonstrate that ethyl tert-butyl ether (ETBE) can be prepared continuously in 40–70% yield and 65–95% selectivity in one-step from ethanol (EtOH) and tert-butanol (tBA) using a macroreticular acid resin catalyst, such as Rohm and Haas'AMBERLYST® 15 having an acidity capacity of 4.7 meq/g or AMBERLYST® 35 having an acidity capacity of 5.2 meq/g at 70°–140° C. and 100 to 500 psig. Other acid resin catalysts that may be used are Dow's Dowex M-31 having an acidity of 4.9 meq/g, Dow's DOWEX® MONOSPHERE M-31, having a uniform bead size of 500 micron ±50, and an acidity capacity of >4.5 meq/g, AMBERLYST® 18 having an acidity of 5.4 meq/g, DOWEX® MONOSPHERE M-31 type and XUR-1525-L94-014, having a uniform bead size of ca. 680 microns. Acidic zeolite catalysts such as ZSM-5 require a slightly higher temperature, from about 100° to 190° C.

In another embodiment of the instant invention good results were also realized using certain crystalline aluminosilicate zeolites, optionally with a binder, as catalysts for the reaction represented in Eq. 1. Particularly effective were the isostructural group of pentasil zeolites.

As mentioned, Ward, supra, p 271 provides an overview of the structure of pentasils. These zeolites, as well as silicalite have $SiO_2$—$Al_2O$ ratios greater than 10. Silicalite, ZSM-5, ZSM-11 and related materials have structures with ten-ring channel systems in contrast with the eight-membered zeolites such as A and erionite and the twelve-membered systems such as zeolites X and Y.

Pentasil zeolites are hydrophobic compared with A, X and Y zeolites. ZSM-5 has orthorhombic unit cells, whereas ZSM-11 is tetragonal.

The pentasil structures are very thermal and acid stable. They are synthesized in the presence of ammonium ions, which become an integral part of the structure. Heating up to 600° C. decomposes the organic cations leaving the highly porous structure.

Other ZSM series zeolites are not considered to be pentasils. ZSM-21, ZSM-35 and ZSM-38 are considered to be of the ferrierite type zeolite. ZSM-20 is considered of the faujasite type and ZSM-34 is considered to be of the offretite/erionite group. Whyte, supra, p. 571.

Medium pore, pentasil-type zeolites having 10-membered oxygen ring systems include, for example, ZSM-5, ZSM-11, ZSM-22, ZSM-23, ZSM-48 and laumontite. Their framework structures contain 5-membered oxygen rings and they are more siliceous than previously known zeolites. In many instances these zeolites may be synthesized with a predominance of silicon and with only a very small concentration of other atoms such as aluminum; thus, these zeolites may be considered as "silicates" with framework substitution by small quantities of other elements such as aluminum. Among the zeolites in this group, only ZSM-5 and ZSM-11 have bidirectional intersecting channels, the others have nonintersecting unidirectional channels.

The medium-pore pentasils, unlike other zeolites, have pores of uniform dimension and have no large supercages with smaller size windows. This particular feature is believed to account for their unusually low coke-forming propensity in acid-catalyzed reactions. Because the pentasil zeolites are devoid of the bottle-necks in the window/cage structure, molecules larger than the size of the channel do not form with the exception perhaps at the intersections.

The preferred forms of pentasil zeolite are the highly acidic, high silica forms, having silica-to-alumina mole ratio of at least 30:1, and preferably in the range of 30:1 to 350:1 in the as-synthesized form. A narrower range of 50:1 to 150:1 is preferred and the pentasil zeolites demonstrated in the examples possess $SiO_2/Al_2O_3$ ratios of about 30:1 to ca. 350:1.

Generally, it can be said that changes in the Si/Al ratio from one to infinity result in predictable changes in:

Stability, from <700° C. to ~1300° C.

Surface selectivity, from hydrophilic to hydrophobic

Acidity increasing in intrinsic strength

Cation concentration decreasing

Structure from 4-, 6 - and 8-rings to 5-rings.

See "Industrial Catalytic Applications of Molecular Sieves" by P. R. Pujadó, et al. in CATAL. TODAY, 13, 113–141 (1992).

The thermal stability of the crystalline lattice of zeolites varies substantially, from about 700° C. for aluminum-rich zeolites, to about 1300° C. for silicalite. Aluminum-rich zeolites are unstable in the presence of acids, while silicon-rich zeolites are stable even in concentrated mineral acids. In contrast, silicon-rich zeolites exhibit low stability in basic solutions. Likewise, aluminum-rich zeolites exhibit a highly-polar hydrophilic surface. Silicon-rich zeolites tend to be more nonpolar and hydrophobic. The onset of hydrophobicity appears to occur at a Si/Al ratio of about 10.

The silica-to-alumina ratios referred to in this specification are the structural or framework ratios, that is, the ratio of the $SiO_4$ to the $AlO_4$ tetrahedra, which together constitute the structure of which the zeolite is composed. It should be understood that this ratio may vary from the silica-to-alumina ratio determined by various physical and chemical methods. For example, a gross chemical analysis may include aluminum which is present in the form of cations associated with the acidic sites on the zeolite, thereby giving a low silica-to-alumina ratio. Similarly, if the ratio is determined by the thermogravimetric analysis (TGA) of ammonia desorption, a low ammonia titration may be obtained if cationic aluminum prevents exchange of the ammonium ions onto the acidic sites. These disparities are particularly troublesome when certain treatments, such as dealuminization, which result in the presence of ionic aluminum free of the zeolite structure, are employed. Due care should therefore be taken to ensure that the framework silica-to-alumina ratio is correctly determined.

The silica-to-alumina ratio of the zeolite may be determined by the nature of the starting materials used in its preparation and their quantities relative one to another. Some variation in the ratio may therefore be obtained by changing the relative concentration of the silica precursor relative to the alumina precursor, but definite limits in the maximum obtainable silica-to-alumina ratio of the zeolite need be observed. For a pentasil zeolite, this limit is usually about 350:1 (although higher ratios may be obtained) and for ratios above this value, other methods are usually necessary for preparing the desired high silica zeolite. This method generally comprises contacting the zeolite with an acid, preferably a mineral acid such as hydrochloric acid.

Example 7 demonstrates the use of acidic ZSM-5 as a catalyst in the instant invention.

The feed in the instant invention can contain a molar ratio of EtOH to tBA from 1:1 to 10:1. Usually the molar ratio would be in the range of 1:1 to 4:1. The preferred molar ratio is 1.5:1 to 2.0:1.

The process can be run with water in the feed: therefore, rigorous drying of the feed (and/or recycle streams) dehydration of the t-butanol to isobutylene in a separate reactor to further react with ethanol as in U.S. Pat. No. 5,333,333 is not necessary. Water can also be present in the feed at 1 to 5 wt %. However, the best tBA conversions are achieved when there is less water in the feed. Less than 5% water is desirable in order to achieve 70% tBA conversion.

The liquid hourly space velocity can range from 0.1 to 20 (or greater) with LHSV 1 to 4 preferred.

Suitable conditions for the instant invention include mild temperatures. Etherification can generally be conducted at temperatures from 20° to 150° C.; the preferred range using a macroreticular acid resin catalyst is 80° to 140° C. Good results are observed throughout this temperature range.

However, it can be noted that the best tBA conversion figures are observed when the temperature is less than 100° C. A macroreticular acid resin catalyst, such as Rohm and Haas' AMBERLYST® 15 and AMBERLYST® 35 can be used as the catalyst at 40°–140° C. (preferably 90° to 120° ) and 100 to 500 psig. The preferred temperature range using acidic zeolites is 100° to 190° C. The total operating pressure may be from 0 to 1000 psig, or higher. The preferred pressure range is 50 to 500 psig. Acidic zeolite catalysts such as ZSM-5 can also be used in this process for 100° to 190° C. at 100 to 500 psig.

The tBA conversion will range from 40 to 70% and the ETBE selectivity ranged from 65% to 95% under the preferred conditions. Tables A and B present the conditions for achieving tBA conversions of 50%, 55% and 60%, using AMBERLYST® 15 as catalyst.

Other examples of acid resin catalysts that may be used, under similar conditions, in this process are macroreticular resins with uniform bead sizes, such as DOW's DOWEX® MONOSPHERE M-31 (bead size 500±50 microns) and XUR-1525-L94-014 (bead size ca. 680 microns).

TABLE A

EXAMPLE 2: Experimental Design 1
Lowest Temperature Optimization of tBA Conversion

| tBA Conversion (%) | ETBE Selectivity (%) | Temperature (°C.) | EtOH:tBA Molar Ratio | Water (wt %) | LHSV |
|---|---|---|---|---|---|
| 50.2 | 76.0 | 100 | 1.1 | 4.9 | 4.0 |
| 55.0 | 68.0 | 116 | 1.2 | 4.9 | 4.0 |
| 60.0 | 73.7 | 116 | 1.9 | 4.9 | 4.0 |

Ranges Tested: Temperature 100°–120° C.; 4.9 wt % water; LHSV 1–4%; EtOH:tBA molar ratio 1.1–2.0, AMBERLYST ® 15 as catalyst.

Figure 1:
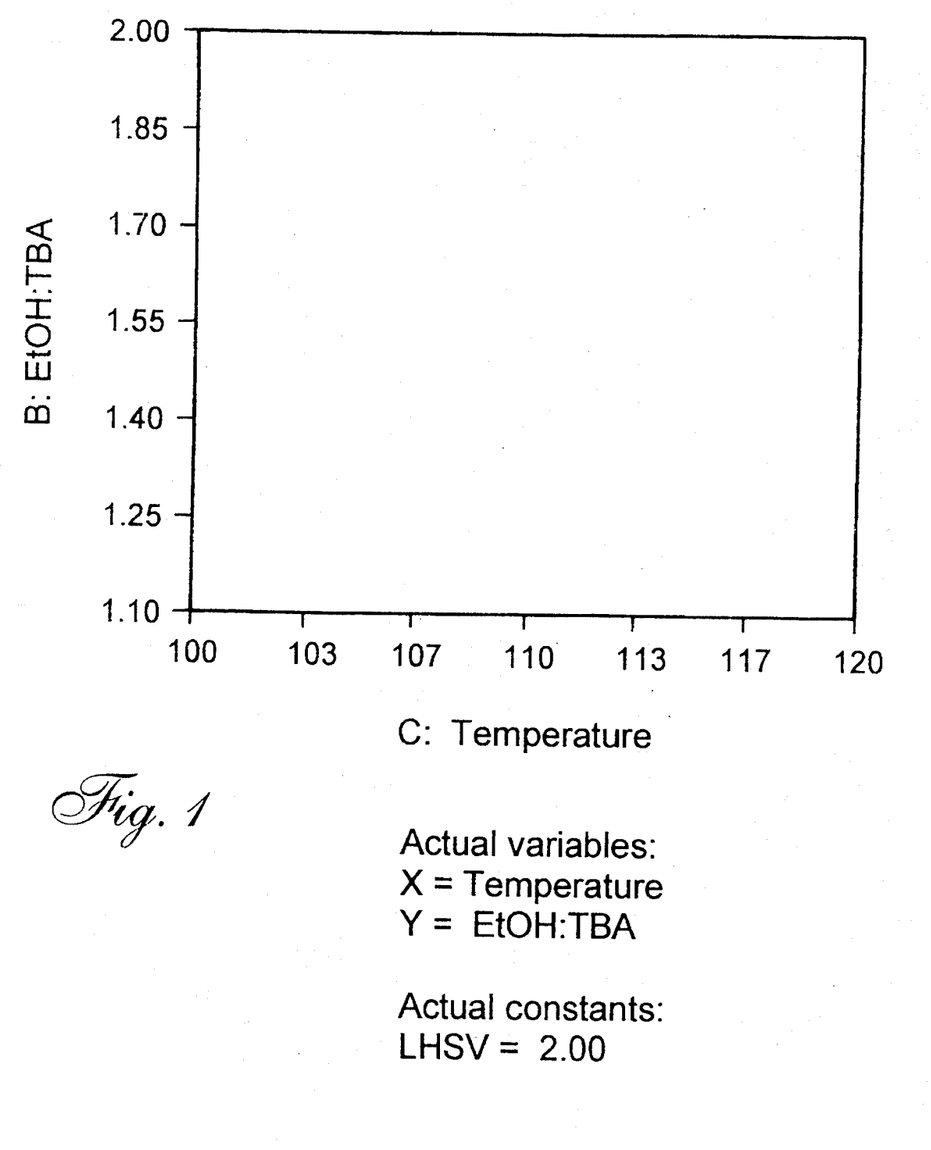
FIGS. 1, 2 and 3 demonstrate conditions which will give 50, 55 and 60% tert-butyl alcohol conversion respectively. Shaded portions of figures represent conditions which will not give the desired TBA conversion.
Figure 2:
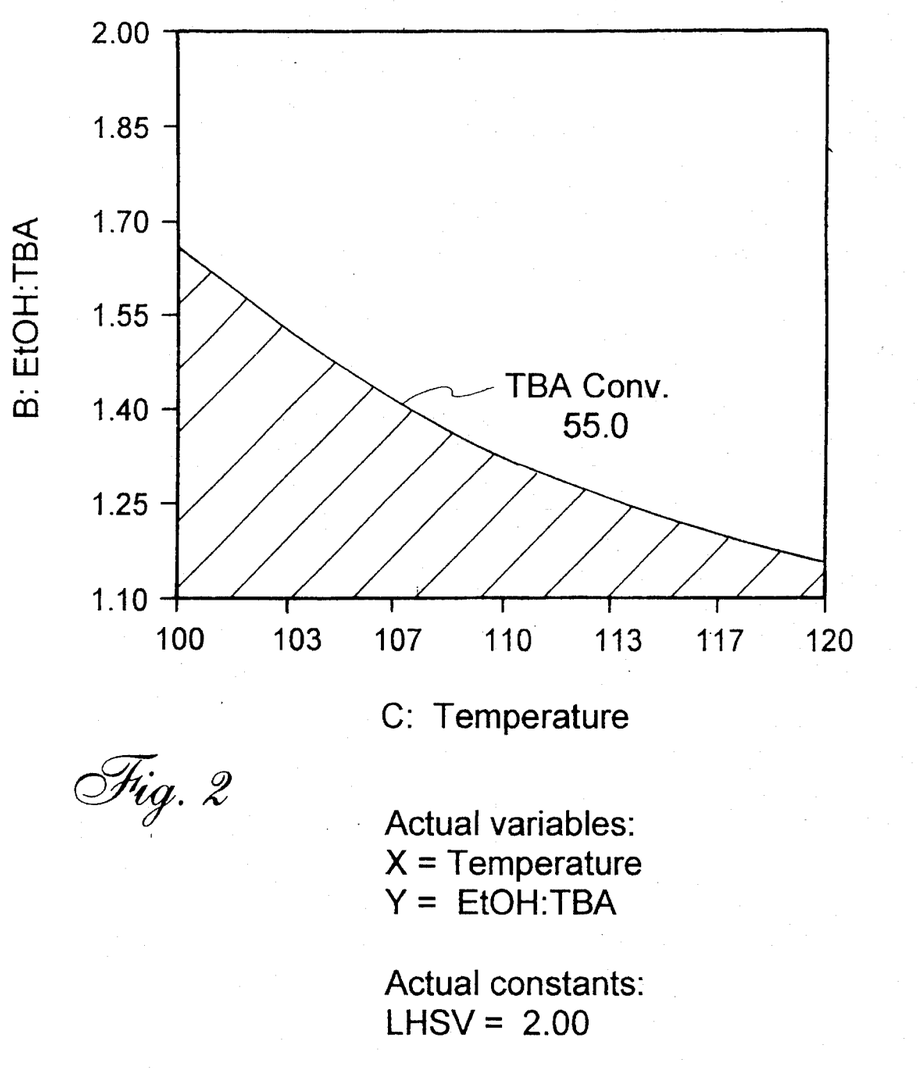
Figure 3:
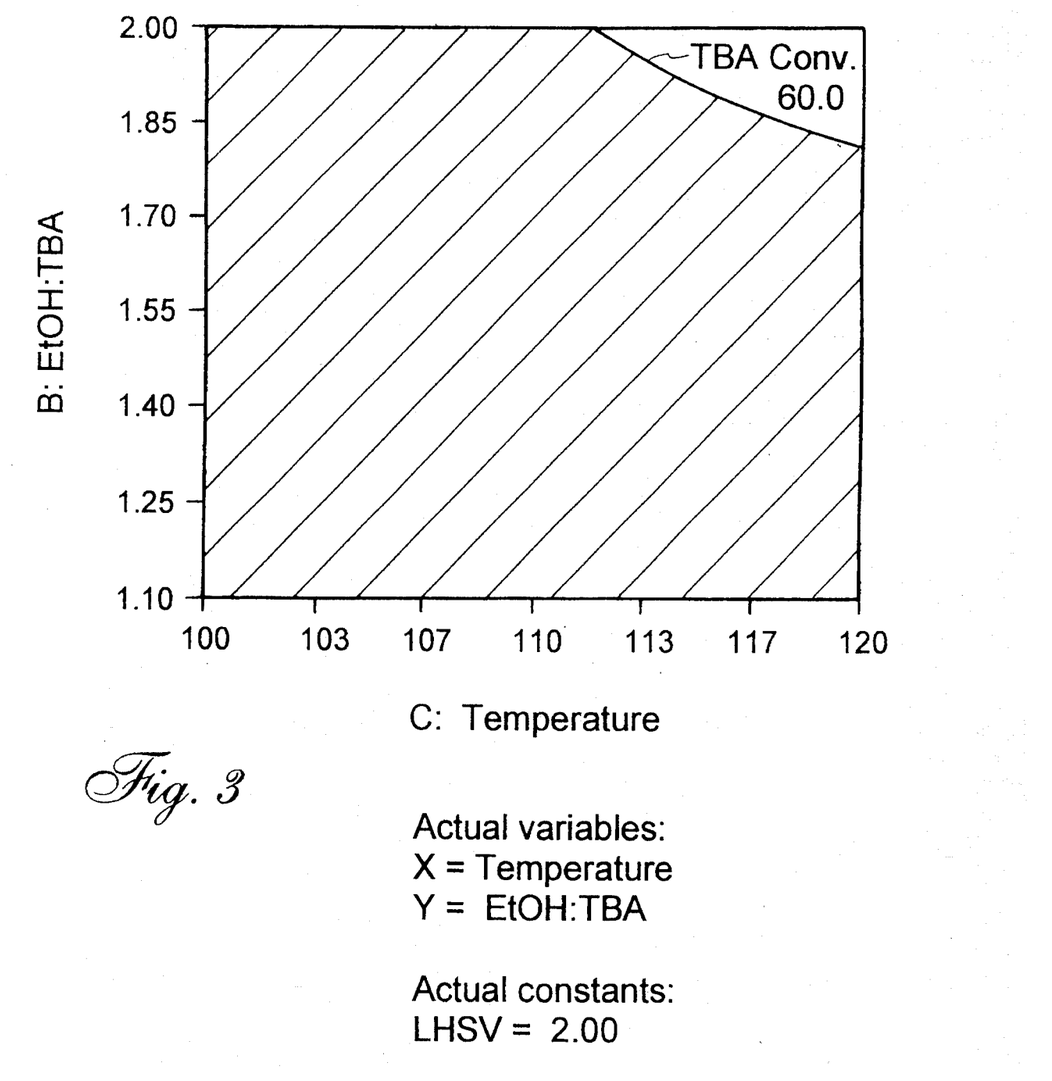

FIGS. 1, 2 and 3 demonstrate conditions which will give 50%, 55% and 60% tBA conversion respectively. Shaded portions of figures represent conditions which will not give the desired tBA conversion.

TABLE B

EXAMPLE 2: Experimental Design 1
Lowest Temperature Optimization of tBA Conversion

| tBA Conversion (%) | ETBE Selectivity (%) | Temperature (°C.) | EtOH:tBA Molar Ratio | Water (wt %) | LHSV |
|---|---|---|---|---|---|
| 50.0 | 89.3 | 77 | 1.3 | 2.1 | 1.0 |
| 55.0 | 87.9 | 90 | 1.4 | 2.1 | 1.0 |
| 58.9 | 88.3 | 90 | 1.5 | 1.0 | 1.0 |

Ranges Tested: Temperature 50°–90° C.; 1.5 wt % water; LHSV 0.25–1.0%; *60% tBA conversion was not achievable using the given range conditions, using AMBERLYST ® 15 as catalyst.

Figure 4:
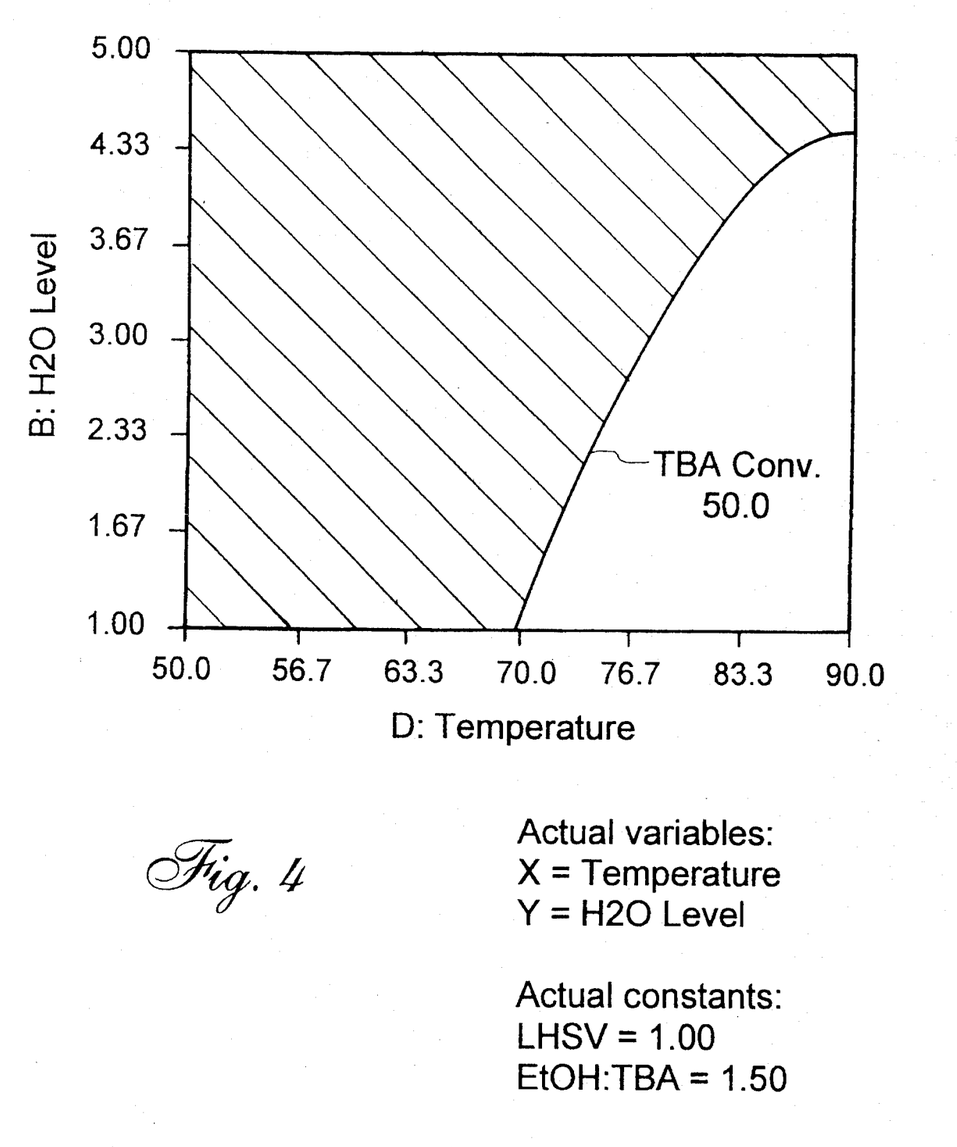
FIGS. 4 and 5 demonstrate the water and temperature dependence of tertiary butyl alcohol conversion.
Figure 5:
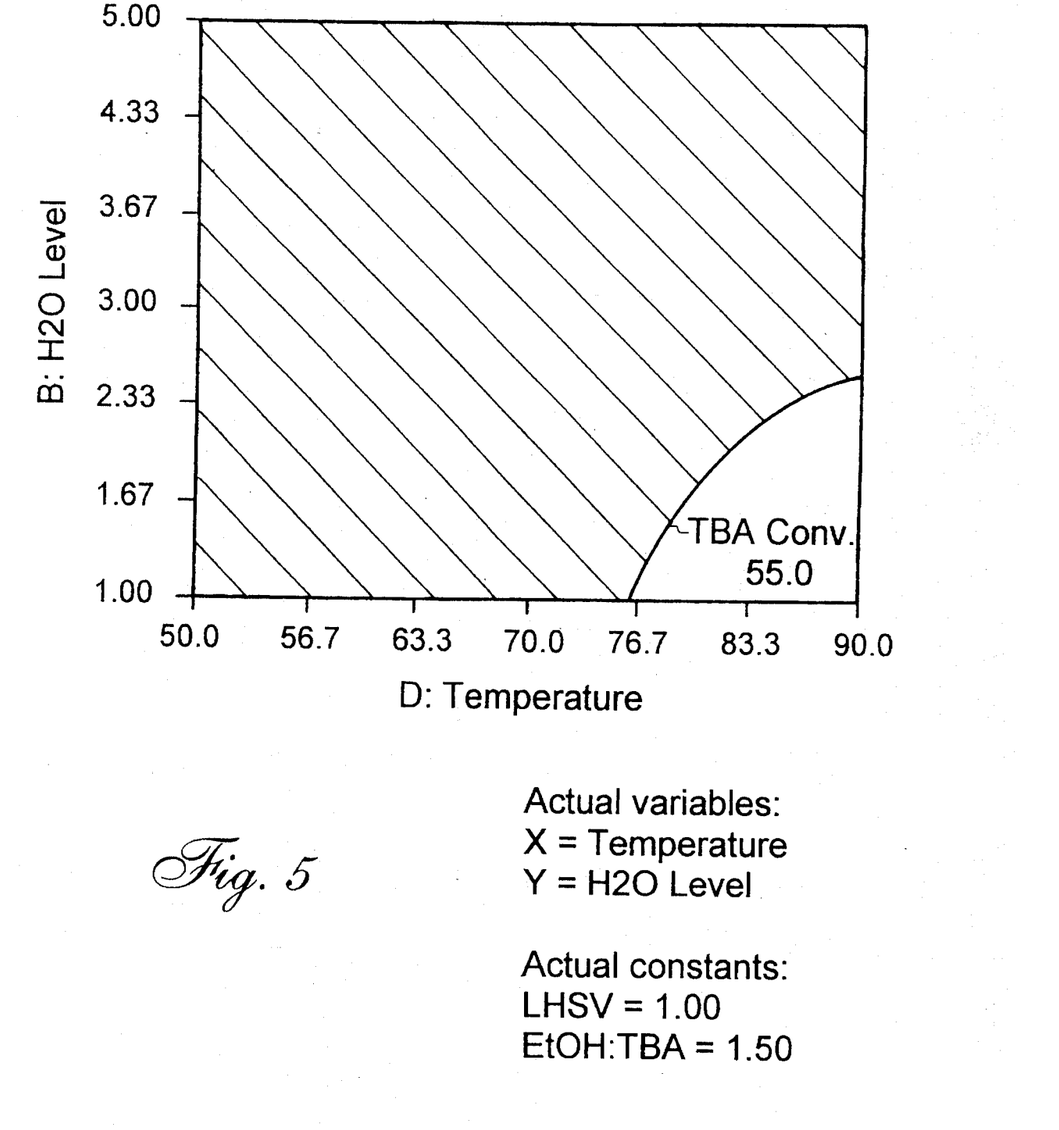

FIGS. 4 and 5 demonstrate the water and temperature dependence of tBA conversion. 60% tBA conversion is not achievable at greater than 1% water at LHSV 1.0 with EtOH to tBA molar ratio of 1.5.

Figure 6:
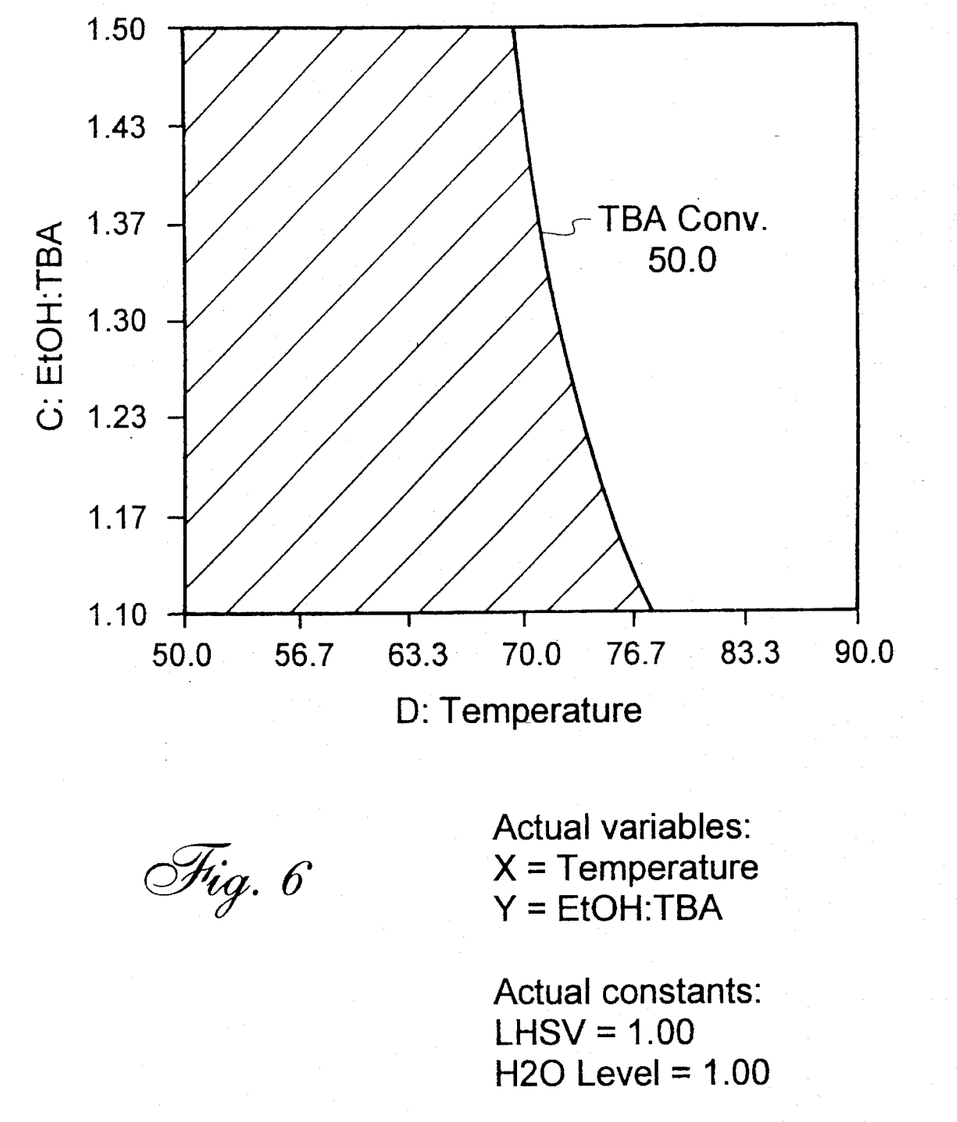
FIGS. 6, 7 and 8 demonstrate the dependence of tertiary butyl alcohol conversion on the ethanol to tertiary butyl alcohol ratio at different water levels.
Figure 7:
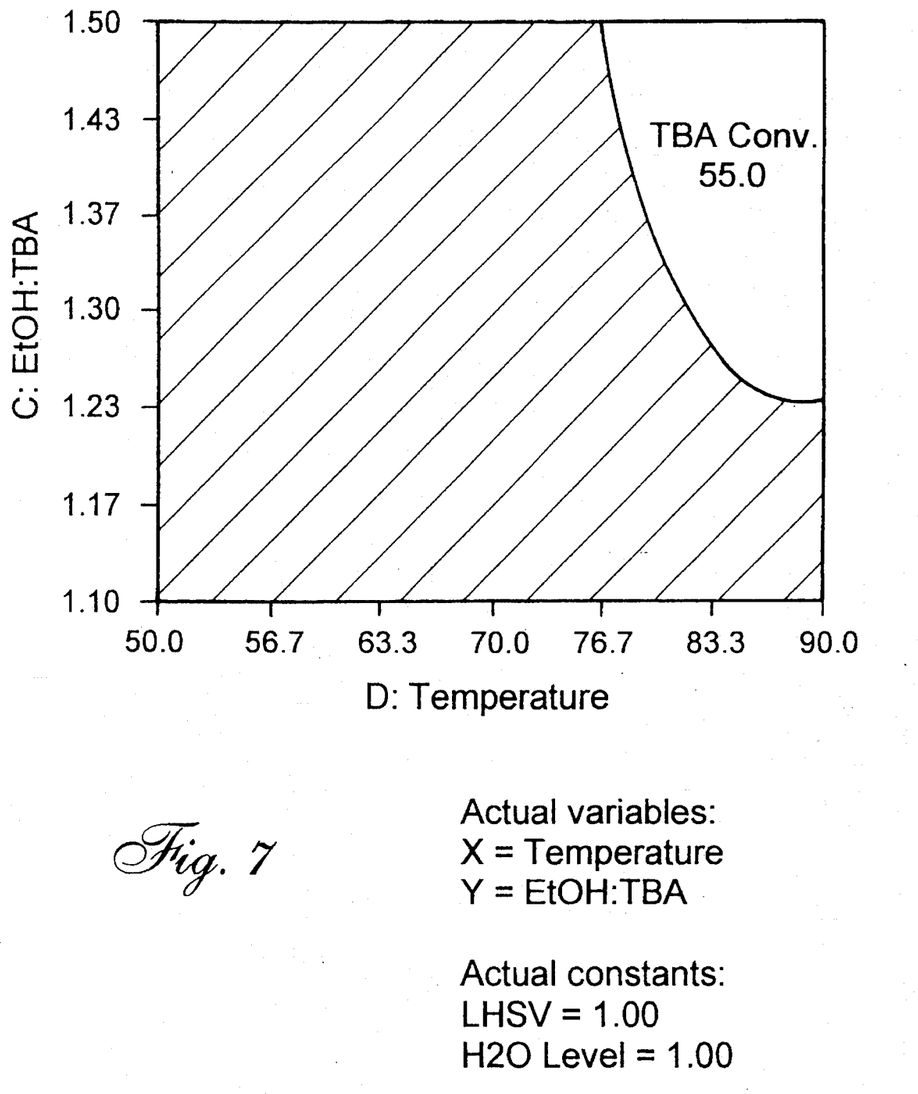
Figure 8:
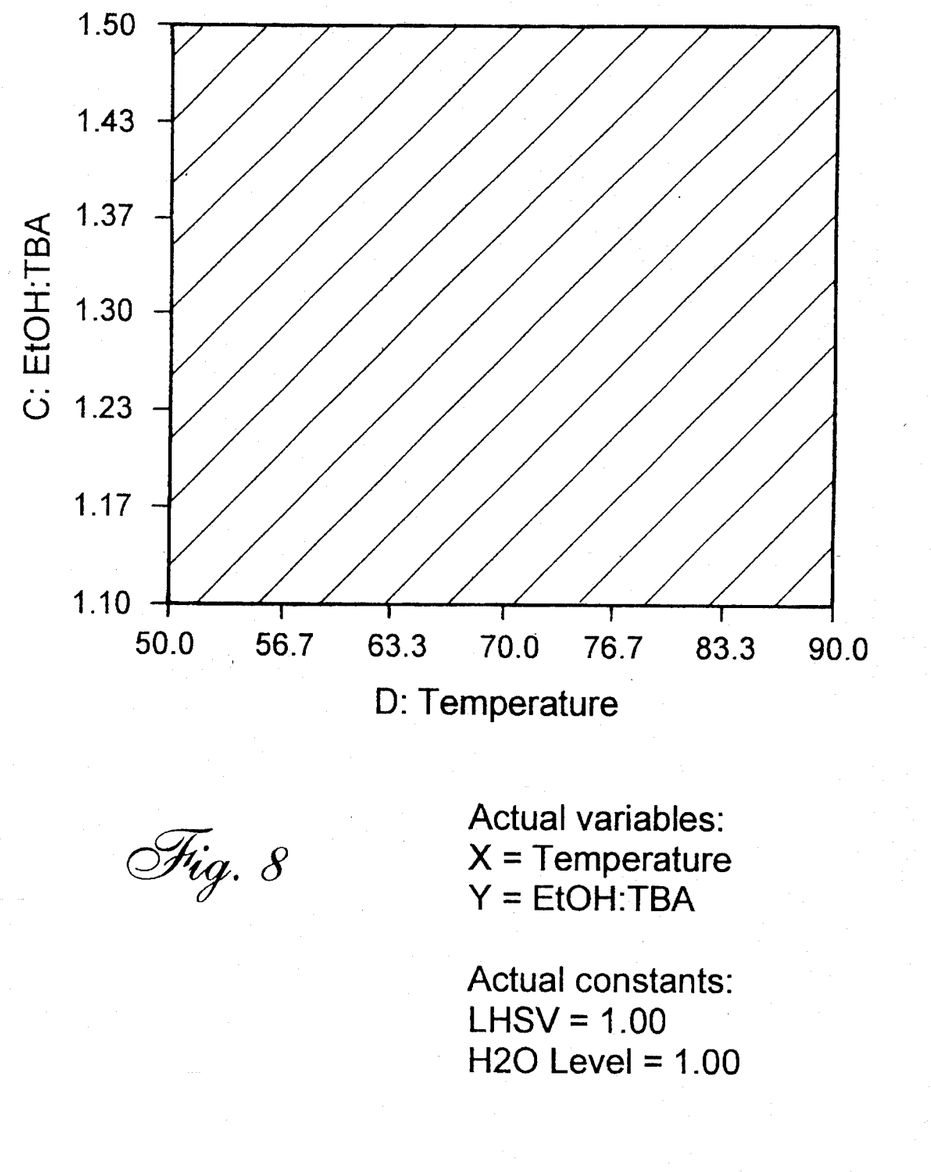

FIGS. 6, 7 and 8 demonstrate the dependence of tBA conversion on the EtOH to tBA ratio and temperature at different water levels. 60% tBA conversion is not achievable at 1% water and LHSV 1.0 no matter what the temperature or EtOH to tBA molar ratio was.

Figure 9:
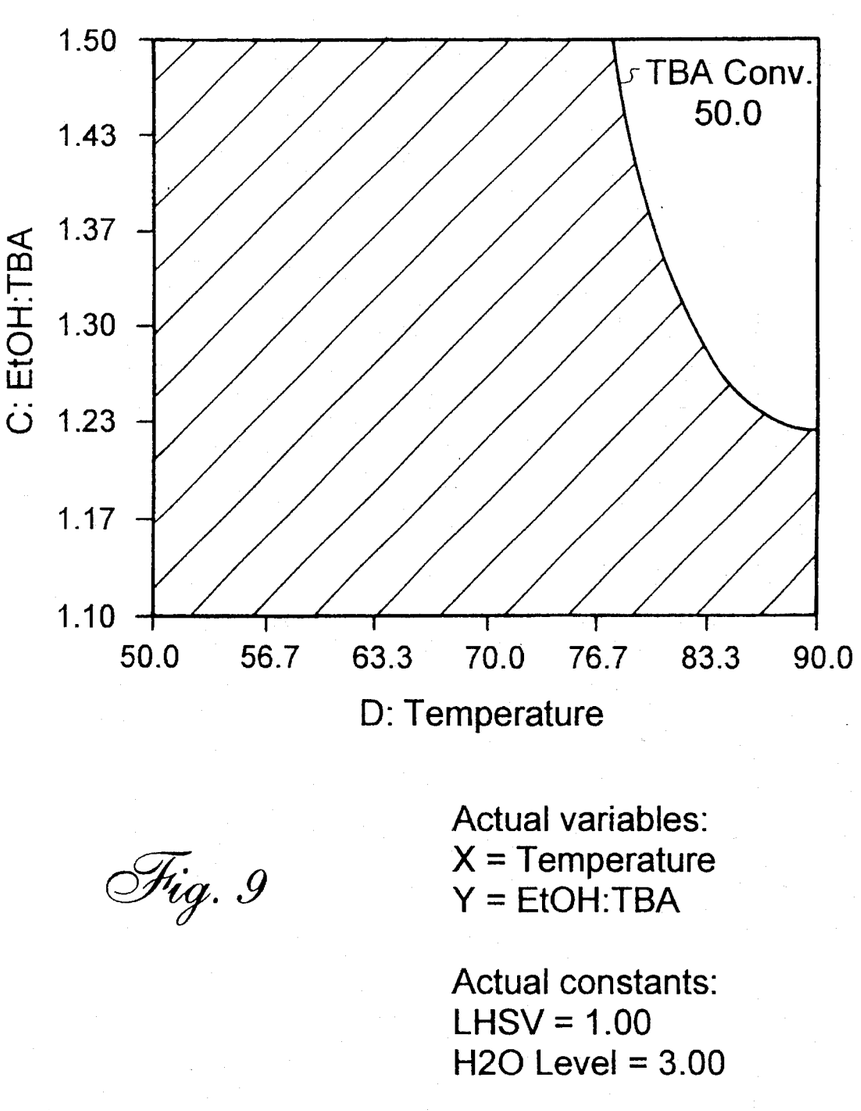
FIGS. 9 and 10 demonstrate the dependence of tertiary butyl alcohol conversion, at 3 and 5 wt % water in the feed respectively, when varying the ethanol to tertiary butyl alcohol ratio and temperature.
Figure 10:
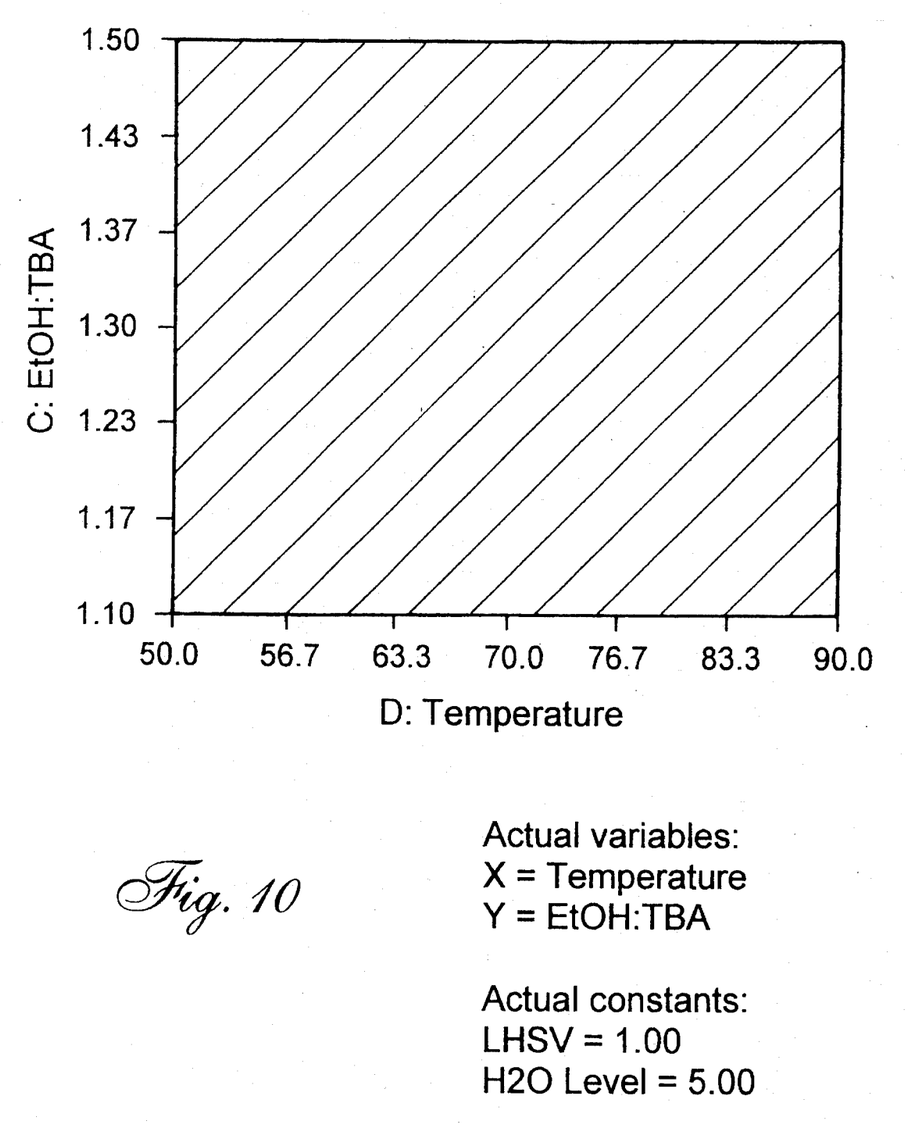

FIGS. 9 and 10 demonstrate the dependence of tBA conversion, at 3 and 5 wt % water in the feed respectively, when varying the EtOH to tBA ratio and temperature. 55% tBA conversion is not achievable at 3% water and LHSV 1.0 no matter what the temperature or EtOH to tBA molar ratio were (FIG. 9). 50% tBA conversion is not achievable at 5% water in the feed and LHSV 1.0 no matter what the temperature or EtOH to tBA molar ration was (FIG. 10).

The reaction may be carried out in either a stirred slurry reactor or in a fixed bed continuous flow reactor. The catalyst concentration should be sufficient to provide the desired catalytic effect.

Typically, ETBE is generated continuously in up to ca. 50 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (tBA, wt %) are estimated in the following examples using the equation:

$$\frac{(\text{Mole \% of tBA in Feed} - \text{Mole \% of tBA in Product})}{\text{Mole \% of tBA in Feed}} \times 100$$

Selectivities to ETBE are estimated in the following examples by the equation:

$$\frac{\text{Moles of ETBE Product}}{(\text{Moles of ETBE} + \text{Moles of Isobutylene} + \text{Moles of Diethyl Ether})}$$

The examples which follow illustrate the one-step synthesis of ETBE from tBA and or EtOH (Eq. 1) using macroreticular acidic resins or pentasil zeolites.

In particular, Examples 1 to 5 illustrate the following features of the instant invention:

1. Very high ETBE selectivities (≦90%) are attainable at low temperatures (<100° C.)
2. The equilibrium concentration of products and reactants is highly dependent on the concentration of water. The best tBA conversions are achieved when there is less water in the feed Low water, i e <<5 preferably below 1%, in the feed is desirable in order to achieve at least 65% tBA conversion at 90°–120° C.
3. Diethyl ether production can be limited to <3000 ppm at temperatures less than 120° C.
4. Space velocity becomes a factor in tBA conversion and ETBE selectivity at low temperatures.
5. High EtOH to tBA ratio (>1.5) are desired in order to increase both the tBA conversion (≧55%) and ETBE selectivity (≧65%).

The examples are only intended as a means of illustration and it is understood the invention is not meant to be limited thereby.

TABLE 1

List of One-Step ETBE Experimental Runs

| Ex. No. | Notebook No. | Catalyst | Temperature Range (°C.) | LHSV Range | Wt % Water Range | EtOH to tBA Ratio Range |
|---|---|---|---|---|---|---|
| 1 | 6999-64 | AMBERLYST® 15 | 100–120 | 2 | 4.9 | 2.0 |
| 2 | 6998-51 thru 6998-68 | AMBERLYST® 15 | 100–120 | 1–4 | 4.9 | 1.1–2.0 |
| 3 | 6999-75 | AMBERLYST® 15 | 110 | 2 | 2.5 | 2.0 |
| 4 | 7270-1 thru 7270-27 | AMBERLYST® 15 | 50–90 | 0.25–1.0 | 1–5 | 1.1–1.5 |
| 5 | 7270-28 | AMBERLYST® 15 | 100–120 | 2.0 | 5.0 | 1.5 |
| 6 | 6998-69 | AMBERLYST® 35 | 100–140 | 2 | 4.9 | 2.0 |
| 7 | 6998-71 | ZSM-5 | 100–190 | 2 | 4.9 | 2.0 |
| 8 | 6998-72 | DOWEX® MONOSPHERE M-31 | 110–115 | 2 | 5.0 | 1.5 |
| 9 | 7270-29 | DOW XUR-1525-L94-014 | 90–120 | 1 | 5.0 | 1.5 |

EXAMPLE 1

An initial temperature scan trial, run number 6999–64, was made to test the applicability of a one-step process for producing ethyl t-butyl ether (ETBE) in one step from ethanol (EtOH) and tert-butanol (tBA). A 100 cc electrically heated, upflow reactor charged with cc of AMBERLYST® 15, which had been presoaked in ethanol, was operated at 300 psig and LHSV 2 using a simulated feed. This feed was composed of 49.0% EtOH, 38.8% tBA, 4.0% water, 4.7% isopropanol (IPA) and 0.4% acetone. This provided a 2:1 molar ratio of EtOH to tBA in the feed.

The catalyst was loaded on top of 50 cc of 6 mm glass beads. This served as a preheater for the feed. In front of the reactor and after the feed pump was an unheated guard bed consisting of 50 cc of AMBERLYST® 15 in order to protect the reactor from any inadvertent impurities. The temperature of the reactor was varied from 100° to 120° C. Table 2 gives a listing of the samples, the temperatures at which they were acquired and the respective tBA conversions and ETBE selectivities.

TABLE 2

Notebook No. 6999-64
tBA Conversion and ETBE Selectivity at Different Temperatures in the One-Step ETBE Process with AMBERLYST® 15 as Catalyst at 300 psig and LHSV 2

| Sample # | Temperature (°C.) | tBA Conversion (%) | ETBE Selectivity (%) |
|---|---|---|---|
| 6999-64-1 | 100 | 41.9 | 75.2 |
| 6999-64-3 | 110 | 45.7 | 69.0 |
| 6999-64-5 | 120 | 48.4 | 61.7 |

The feed comprised primarily EtOH to tBA in a 2:1 molar ratio with 4.9 wt % water.

The tBA conversions for the ETBE process turned out to be 41–48% when using AMBERLYST® 15 as the catalyst. The ETBE selectivities were 60–76% when using AMBERLYST® 15 catalyst.

EXAMPLE 2

A 3 level, 3 factorial statistical design experiment was undertaken in order to evaluate the effects of space velocity, ratio of EtOH to tBA in the feed and temperature on the conversion of tBA and ETBE selectivity in the One-Step ETBE process (notebook numbers 6998–51 through 6998–68).

Higher tBA conversions were achieved at higher temperatures and higher ratios of EtOH to tBA in the feed. Higher ETBE selectivity was achieved at lower temperatures (100° C) and higher ratios (2.0:1) of EtOH to tBA in the feed. Space velocity had little or no effect on the two responses.

The tBA conversions of the runs were between 48–60% and the ETBE selectivities were between 65–87% depending upon the EtOH to tBA ratios and the temperatures.

A quadratic model was selected for both tBA conversions and ETBE selectivity. The optimal conditions were at LHSV 2.4, 109° C. and 300 psig using a 2:1 molar ratio of EtOH to tBA and 4.9% water in the feed. These conditions are predicted to give 59.4% tBA conversion with 80.0% ETBE selectivity.

The unrestricted optimal conditions were at LHSV 4.0, 120° C. and 300 psig using a 2:1 molar ratio of EtOH to tBA and 4.9% water in the feed. These conditions are predicted to give 61.4% tBA conversion with 71.3 ETBE selectivity.

EXAMPLE 3

A mixture of one-step ETBE feed with only 2.5% water was tried in order to investigate the effect water would have upon tBA conversion and ETBE selectivity. The feed had a 2:1 molar ratio of EtOH to tBA.

A 100cc electrically heated, upflow reactor charged with 50cc of AMBERLYST® 15, which had been presoaked in EtOH, was operated at 300 psig, 110° C. and LHSV 2. For run number 6999–75 the catalyst was loaded on top of 50cc of 6mm glass beads. The glass beads served as a preheater for the feed. In front of the reactor and after the feed pump was placed an unheated guard bed loaded with 50 cc of AMBERLYST® 15 in order to protect the reactor from any inadvertent impurities.

The tBA conversion was 58.5% and the ETBE selectivity was 80.2%. These results demonstrate the benefit in tBA conversion and ETBE selectivity with less water in the feed.

EXAMPLE 4

Another experimental design involving the conversion of tBA and EtOH in the one-step ETBE process was undertaken. The factors that were examined for an effect on the tBA conversion and ETBE selectivity were temperature, space velocity and EtOH to tBA ratio; also included was a more extensive investigation of the effect of the water level in the feed. AMBERLYST® 15 was again the catalyst for these experiments.

In this design, LHSV, EtOH to tBA ratio, temperature and water level were explored to see if the conversion of tBA and EtOH to ETBE could be improved over the results of the first experimental design. The temperatures (50°–90° C.), space velocities (0.25–1.0) and EtOH to tBA ratios (1.1–1.5) were lower than those examined in the first experimental design of this process, Example 2. In addition the water level was to be varied from 1 to 5% instead of being held constant as in Example 2.

This experimental design, Notebook No. 7270-1 through 7270-27, was conducted in a 50 cc electrically heated, upflow reactor at 300 psig. Nine feeds of various composition, comprising mainly EtOH and tBA, were used. After the feed pump, and before the reactor, was an unheated guard bed filled with 25 cc of the AMBERLYST® 15 catalyst to protect the main bed of catalyst from impurities in the feed.

Quadratic models were again selected for both the optimization of tBA conversion and ETBE selectivity.

The optimal conditions were at LHSV 1.0, 90° C. and 300 psig using a 1.5:1 molar ratio of EtOH to tBA and 1.0% water in the feed. These conditions are predicted to give 58.7% tBA conversion with 88.3% ETBE selectivity.

It is apparent from the results of both experimental designs (Examples 2 and 4) that high temperatures ($\geq 100°$ C.) and low water (<1 wt %) are necessary in order to get 70% tBA conversion.

EXAMPLE 5

AMBERLYST® 15 catalyst was examined, using optimized feed and reactor conditions as determined by the experimental designs and design limitations, in a temperature scan test of the one-step ETBE process.

The catalyst test, Notebook No. 7270-28 was conducted in a 50 cc electrically heated, upflow reactor at 300 psig and LHSV 2.0 using a feed comprising primarily EtCH and tBA in a 15:1 molar ratio There was also 5 wt % water 4 8% IPA, 14% MEK and 0.3% acetone in this feed. The temperature of the reactor was varied between 100° and 120° C. After the feed pump and before the reactor, was an unheated guard bed filled with AMBERLYST® 15 catalyst in order to protect the main catalyst bed from inadvertent impurities in the feed.

The AMBERLYST® 15 catalyst displayed a tBA conversion of 47.0% and ETBE selectivity of 83.2% at 100° C. The tBA conversion and ETBE selectivity are very close to what is predicted by the one-step ETBE experimental design.

The results are presented in Table 3 below.

TABLE 3

Notebook No. 7270-28
t..A Conversion and ETBE Selectivity at Different
Temperatures in the
One-Step ETBE Process with AMBERLYST ® 15 as Catalyst
at 300 psig and LHSV 2

| Temperature (°C.) | tBA Conversion (%) | ETBE Selectivity (%) | Diethyl Ether Level (ppm) |
| --- | --- | --- | --- |
| 100 | 50.6 | 81.3 | 2540 |
| 105 | 51.0 | 78.0 | 2490 |
| 110 | 52.6 | 76.5 | 2500 |
| 115 | 52.5 | 72.1 | 2510 |
| 120 | 54.2 | 71.2 | 2540 |

The feed comprised primarily EtOH to tBA in a 1.5:1 molar ratio with 5.0 Wt % water.

EXAMPLE 6

Since higher temperatures appear to enhance the tBA conversion in the presence of EtOH, a second resin catalyst with high temperature capability was explored as a potential candidate.

A sulfonated acid resin catalyst from Rohm and Haas, AMBERLYST® 35 was tried in ETBE production from EtOH and tBA. This catalyst has an acidity capacity of 5.2 meq/g and higher sulfonation than AMBERLYST® 15. This provides higher cross-linking for greater thermal stability and a greater number of acid functionalities in this resin catalyst.

This example is similar to Example 1 except that AMBERLYST® 35 was the catalyst and the temperature scan was from 100° to 140° C.

A 100 cc electrically heated, upflow reactor charged with 50 cc of AMBERLYST® 35, which had been presoaked in ethanol was operated at 300 PSIG and LHSV 2. For Run No. 6998-69 the catalyst was loaded on top of 50 cc of 6 mm glass beads. The glass beads served as a preheater for the feed. In front of the reactor and after the feed pump was placed an unheated guard bed loaded with 50 cc of AMBERLYST® 35 in order to protect the reactor from any inadvertent impurities. A 2:1 molar ratio of ethanol to t-butanol with 5.5% water, 4.9% isopropanol, 1.4% methyl ethyl ketone and 0.3% acetone added as impurities was used as feed. The temperature of the reactor was varied from 100° to 140° C.

Results are presented in Table 4 below.

TABLE 4

Notebook No. 6998-69
tBA Conversion and ETBE Selectivity at Different
Temperatures in the
One-Step ETBE Process with AMBERLYST ® 35 as Catalyst
at 300 psig and LHSV 2

| Temperature (°C.) | tBA Conversion (%) | ETBE Selectivity (%) | Diethyl Ether Level (ppm) |
| --- | --- | --- | --- |
| 100 | 59.7 | 83.8 | 320 |
| 110 | 57.3 | 79.4 | 740 |
| 120 | 59.8 | 74.1 | 2130 |
| 130 | 62.2 | 68.4 | 4210 |
| 140 | 66.2 | 61.5 | 10910 |

The feed comprised primarily EtOH to tBA in a 2:1 molar ratio with 5.5 wt % water.

Although higher tBA conversions were achieved at higher temperatures ($\mp 130°$ C.) there was a significant amount of diethyl ether produced using this catalyst.

EXAMPLE 7

Since higher temperatures appear to enhance the tBA conversion in the presence of EtOH, a zeolite catalyst with high temperature capability was explored as a potential candidate.

This example is similar to Example 1 except that ZSM-5 was the catalyst and the temperature scan was from 100° to 190° C.

A 100 cc electrically heated, upflow reactor charged with 50 cc of ZSM-5 zeolite type catalyst having a silica/alumina ratio of 130. For Run No. 6998-71 the catalyst was loaded on top of 50 cc of 6 mm glass beads. The glass beads serve as a preheater for the feed. In front of the reactor and after the feed pump was placed an unheated guard bed loaded with 50 cc of AMBERLYST® 35 in order to protect the reactor from any inadvertent impurities. A 2:1 molar ratio of EtOH to tBA with 5.5% water, 4.9% isopropanol, 1.4% methyl ethyl ketone and 0.3% acetone added as impurities was used as feed. Temperatures from 100° to 190° C. were explored.

Results are presented in the Table 5 below.

TABLE 5

Notebook No. 6998-71
tBA Conversion and ETBE Selectivity at Different Temperatures
in the One-Step ETBE Process with ZSM-5 as Catalyst
at 300 psig and LHSV 2

| Temperature (°C.) | tBA Conversion (%) | ETBE Selectivity (%) | Diethyl Ether Level (ppm) |
|---|---|---|---|
| 100 | 34.9 | 60.2 | 220 |
| 110 | 47.3 | 66.7 | 440 |
| 120 | 55.2 | 68.5 | 680 |
| 130 | 59.6 | 65.2 | 1480 |
| 140 | 63.8 | 59.6 | 3730 |
| 150 | 66.0 | 54.0 | 8130 |
| 160 | 69.9 | 44.6 | 11950 |
| 170 | 79.3 | 0.3 | 13160 |
| 190 | 91.4 | 0.2 | 29470 |

The feed comprised primarily EtOH to tBA in a 2:1 molar ratio with 5.0 wt % water.

Although higher tBA conversions were achieved when compared to AMBERLYST® 15, at higher temperatures (>140° C.) there was a significant amount of diethyl ether produced using this catalyst.

At temperatures higher than 150° C., diethyl ether (DEE) becomes a major side product and above 160° C the ETBE selectivity decreases substantially. For example, at 190° C. there is 91.4% tBA conversion with only 0.2% ETBE selectivity. In addition, almost 3% DEE is formed.

EXAMPLE 8

Taking into account the results of the two experimental designs of the one-step ETBE process, a lifetime test of a Uniform Particle Size acid resin catalyst from Dow Chemical Company was initiated. The catalyst, DOWEX® MONOSPHERE M-31 has an acidity capacity of >4.5 meq/g and a uniform bead size of 500 microns ±50.

The catalyst test, Notebook No. 6998-72 was conducted in a 100 cc electrically heated, upflow reactor at 300 psig and LHSV 2 using a feed comprising primarily EtOH and tBA in a 1.5:1 molar ratio. There was 5 wt % water in this feed. This reactor configuration also included a guard bed filled with DOW® MONOSPHERE M-31 in order to protect the main bed of catalyst from inadvertent impurities in the feed.

The DOWEX® MONOSPHERE M-31 displayed an initial tBA conversion of 54.2% and ETBE selectivity of 69.3% at 115° C. The initial diethyl ether (DEE) level was 2530 ppm. After 624 hours of continuous operation, the temperature of the reactor was changed from 115° C. to 110° C.

After 1152 hours of continuous operation the tBA conversion was 51.4% and the ETBE selectivity improved to 70.7% at 110° C. The DEE level decreased to 800 ppm.

The results agreed with the results from the first one-step ETBE experimental design, Example 2.

EXAMPLE 9

A temperature scan test of Uniform Particle Size acid resin catalyst from Dow Chemical Company, DOW M-31 type, XUR-1525-L94-014, having a uniform bead size of ca. 680 microns, was tested in the one-step ETBE process.

This example is similar to Example 5 except that DOW XUR-1525-L94-014 was the catalyst and the temperature scan was from 90° to 120° C.

The catalyst test, Notebook No. 7270-29, was conducted in a 50 cc electrically heated, upflow reactor at 300 psig and LHSV 1.5 using a feed comprising primarily EtOH and tBA in a 1.5:1 molar ratio. There was also 5.0 wt % water, 4.7% IPA, 1.4% MEK and 0.3% acetone in this feed. The temperature of the reactor was varied between 90° and 120° C. After the feed pump and before the reactor, was an unheated guard bed filled with DOW XUR-1525-L94-014 catalyst in order to protect the main catalyst bed from inadvertent impurities in the feed.

The DOW XUR-1525-L94-014 catalyst displayed a tBA conversion of 47.0% and ETBE selectivity of 83.2% at 90° C. The tBA conversion and ETBE selectivity are very close to what is predicted by the one-step ETBE experimental design (Example 4).

The results are presented in Table 6 below.

TABLE 6

Notebook No. 7270-29
tBA Conversion and ETBE Selectivity at Different Temperatures
in the One-Step ETBE Process with DOW XUR-1525-L94-014 as
Catalyst at 300 psig and LHSV 1

| Temperature (°C.) | tBA Conversion (%) | ETBE Selectivity (%) | Diethyl Ether Level (ppm) |
|---|---|---|---|
| 90 | 47.0 | 83.2 | NA |
| 95 | 46.6 | 79.6 | NA |
| 100 | 49.2 | 78.0 | NA |
| 105 | 49.4 | 75.2 | 770 |
| 110 | 51.6 | 71.8 | 1400 |
| 115 | 51.7 | 69.5 | 2190 |
| 120 | 54.2 | 63.7 | 3820 |

The feed comprised primarily EtOH to tBA in a 1.5:1 molar ratio with 5.0 wt % water.

What is claimed is:

1. A method for synthesizing ethyl tertiary butyl ether (ETBE) in one step which comprises reacting t-butanol with ethanol in the presence of a catalyst consisting essentially of macroreticular acid resin catalyst and continuously contacting said ethanol and t-butanol in a molar amount of from about 1:1 to 4:1 over said macroreticular resin at a temperature of about 40° C. to 140° C. and a pressure of atmospheric to 500 psig to obtain ethyl tert-butyl ether product.

2. A method as in claim 1 wherein the macroreticular acid resin is typified by the presence of sulfonic acid groups.

3. A method as in claim 2 wherein the macroreticular acid resin is a solid resin of divinyl benzene cross-linked sulfonated polystyrene.

4. A method of claim 2 wherein the macroreticular acid resin has an acidity capacity of 4–6 meq/g.

5. The method of claim 4 wherein the macroreticular acid resin has a uniform bead size.

6. The method of claim 5 wherein the macroreticular acid resin bead size is in the range 400–800 microns.

7. The method of claim 6 wherein the ethanol to t-butanol molar feed ratio is 1.5:1, the operating temperature is 90° C., and the water content in the feed is 1%, wherein t-butanol conversion levels are 55% or greater and the selectivity to desired ethyl t-butyl ether is 85% or greater.

8. A method as in claim 1 wherein the reaction takes place at a temperature of 90° C. to 120° C.

9. A method as in claim 1 wherein the molar ratio of ethanol to tertiary butyl alcohol is 1.5:1 to 2.0:1.

10. A method as in claim 1 further comprising a liquid hourly space velocity of 0.1 to 20.

11. A method as in claim 6 wherein the liquid hourly space velocity is 1 to 4.

12. A method of claim 1 wherein the ethanol plus t-butanol feed contains less than 1% water, the operating temperatures is 90° to 120 ° C. and the achieved t-butanol conversion is 65% or greater.

13. A method of claim 1 wherein the ethanol/t-butanol feed molar ratio is >1.5, the operating temperature is 110°–120° C., the t-butanol conversion is 55% or greater and the ETBE selectivity is 65% or greater.

14. The method of claim 1 wherein the operating temperature is below 100° C. and the ETBE selectivity is 90% or greater.

15. The method of claim 1 wherein the operating temperature is 120° C., or less, and the diethyl ether coproduction is limited to <3000 ppm.

16. The method of claims 1 wherein the ethanol to t-butanol molar feed ratio is 1.5:1, the operating temperature is 90° C., and the water content in the feed is 1%, wherein t-butanol conversion levels are 55% or greater and the selectivity to desired ethyl t-butyl ether is 85% or greater.

17. A method for synthesizing ethyl tertiary butyl ether in one step which comprises reacting t-butanol with ethanol in the presence of a catalyst consisting essentially of an acidic pentasil zeolite and continuously contacting said ethanol and t-butanol in a molar amount of from about 1:1 to 4:1 over said acidic pentasil zeolite at a temperature of about 100° C. to 190° C. and a pressure of atmospheric to 500 psig to obtain ethyl tert-butyl ether.

18. A method as in claim 17 wherein the pentasil zeolite has a silica:alumina molar ratio of 50:1 to 150:1.

19. A method as in claim 18 wherein the pentasil zeolite has a silica:alumina ratio in the range of 120:1 to 150:1.

* * * * *